United States Patent
Shan et al.

(10) Patent No.: US 10,441,173 B2
(45) Date of Patent: Oct. 15, 2019

(54) SYSTEM AND METHOD FOR EXTRACTING PHYSIOLOGICAL INFORMATION FROM REMOTELY DETECTED ELECTROMAGNETIC RADIATION

(71) Applicant: KONINKLIJKE PHILIPS ELECTRONICS N.V., Eindhoven (NL)

(72) Inventors: Caifeng Shan, Eindhoven (NL); Alexander Dubielczyk, Gaertringen (DE); Andreas Wolfgang Schlack, Gaeufelden OT Taiflingen (DE); Rolf Neumann, Calw (DE)

(73) Assignee: KONINKLIJKE PHILIPS ELECTRONICS N.V., Eindhoven (NL)

(*) Notice: Subject to any disclaimer, the term of this patent is extended or adjusted under 35 U.S.C. 154(b) by 684 days.

(21) Appl. No.: 14/135,636

(22) Filed: Dec. 20, 2013

(65) Prior Publication Data
US 2014/0180132 A1   Jun. 26, 2014
US 2017/0325686 A9   Nov. 16, 2017

Related U.S. Application Data

(60) Provisional application No. 61/740,661, filed on Dec. 21, 2012.

(30) Foreign Application Priority Data

Dec. 21, 2012   (EP) ..................................... 12199139

(51) Int. Cl.
*A61B 5/00*   (2006.01)
*G06T 7/00*   (2017.01)
(Continued)

(52) U.S. Cl.
CPC .......... *A61B 5/0059* (2013.01); *G06T 7/0012* (2013.01); *A61B 5/02* (2013.01);
(Continued)

(58) Field of Classification Search
CPC ......... A61B 5/0059; A61B 5/02; A61B 5/024; A61B 5/02416; G06T 2207/30076; G06T 7/0012
See application file for complete search history.

(56) References Cited

U.S. PATENT DOCUMENTS 6,503,206 B1   1/2003   Li et al.
6,540,663 B1   4/2003   Vau et al.
(Continued)

FOREIGN PATENT DOCUMENTS

WO   2005096613 A1   10/2005
WO   2008125995 A1   10/2008
(Continued)

OTHER PUBLICATIONS

Verkruysse, W., et al.; Remote plethysmographic imaging using ambient light; 2008; Opt. Express; 16(26) 21434-21445.

*Primary Examiner* — Amelie R Gillman

(57) ABSTRACT

A system and a related method extract physiological information from remotely detected electromagnetic radiation. The system includes an interface configured for receiving a data stream including image data representing an observed overall region of at least one subject of interest. A partitioning unit defines a plurality of sub regions in the overall region. A classifier classifies the plurality of sub regions into at least one indicative type of region and at least one auxiliary type of region. The at least one indicative type of region includes at least one indicative region of interest at least partially representing the subject of interest. The at least one auxiliary type of region includes at least one reference region. The system further comprises a data pro-
(Continued)

cessor configured for processing at least one sub region classified as region of interest, thereby obtaining vital information.

10 Claims, 6 Drawing Sheets

(51) Int. Cl.
  *A61B 5/024* (2006.01)
  *A61B 5/02* (2006.01)
(52) U.S. Cl.
  CPC ........... *A61B 5/024* (2013.01); *A61B 5/02416* (2013.01); *G06T 2207/30076* (2013.01)

(56) References Cited

U.S. PATENT DOCUMENTS

| | | | |
|---|---|---|---|
| 7,625,344 B1 | 12/2009 | Brady et al. | |
| 2003/0133601 A1* | 7/2003 | Giger | G06T 7/0012 382/128 |
| 2004/0258314 A1* | 12/2004 | Hashimoto | G06F 3/012 382/224 |
| 2005/0063566 A1* | 3/2005 | Beek | A61B 5/0059 382/115 |
| 2005/0119555 A1* | 6/2005 | Fritz | A61B 5/02007 600/410 |
| 2007/0016079 A1 | 1/2007 | Freeman et al. | |
| 2007/0292011 A1* | 12/2007 | Nishimura | A61B 1/00009 382/128 |
| 2008/0294016 A1 | 11/2008 | Gobeyn et al. | |
| 2009/0119841 A1* | 5/2009 | Takashima | A61B 5/11 5/600 |
| 2009/0147999 A1* | 6/2009 | Maeda | A61B 1/00009 382/106 |
| 2009/0185731 A1* | 7/2009 | Ray | G06T 7/0012 382/131 |
| 2010/0061596 A1 | 3/2010 | Mostafavi et al. | |
| 2010/0189323 A1* | 7/2010 | Sakagawa | G06F 19/321 382/128 |
| 2011/0044506 A1* | 2/2011 | Chen | G06T 7/0081 382/103 |
| 2012/0242501 A1* | 9/2012 | Tran | A61B 5/0024 340/870.02 |
| 2013/0215244 A1* | 8/2013 | Mestha | H04N 7/18 348/77 |
| 2013/0331669 A1* | 12/2013 | Berte | G06T 7/0016 600/324 |
| 2014/0303454 A1* | 10/2014 | Clifton | A61B 5/0205 600/301 |

FOREIGN PATENT DOCUMENTS

| | | |
|---|---|---|
| WO | 2010100594 A2 | 9/2010 |
| WO | 2011/021128 | 2/2011 |
| WO | 2011042839 A1 | 4/2011 |
| WO | 2012/066454 | 5/2012 |
| WO | 2012140531 A1 | 10/2012 |
| WO | 2013027027 A2 | 2/2013 |

* cited by examiner

SYSTEM AND METHOD FOR EXTRACTING PHYSIOLOGICAL INFORMATION FROM REMOTELY DETECTED ELECTROMAGNETIC RADIATION

CROSS REFERENCE TO RELATED APPLICATIONS

This application claims the benefit of U.S. provisional application Ser. No. 61/740,661 filed Dec. 21, 2012 and EP provisional application serial no. 12199139.2 filed Dec. 21, 2012.

FIELD OF THE INVENTION

The present disclosure relates to a system and a method for extracting physiological information from remotely detected electromagnetic radiation. More particularly, the present disclosure relates to the detection of vital parameters or, more generally, vital signs information, from electromagnetic radiation re-emitted by a subject of interest. More particularly, but likewise non-restricting, the present disclosure may further relate to the extraction of information from remotely detected electromagnetic radiation which involves, at least in part, visible radiation. Visible radiation may relate to radiation of a particular wavelength range which is visible to a human eye. Even more specifically, the present disclosure may relate to image processing systems and methods for detecting and monitoring vital parameters which can be applied, for instance, in the field of remote monitoring, such as remote photoplethysmographic monitoring, remote oxygen saturation detection and related applications.

The present disclosure further relates to a computer readable non-transitory medium.

BACKGROUND OF THE INVENTION

WO 2010/100594 A2 discloses a method and a system for processing images of at least one living being, including:

obtaining a sequence of digital images taken at consecutive points in time;

selecting at least one measurement zone comprising a plurality of image points, wherein the step of selecting at least one measurement zone includes analyzing information based on pixel data of a plurality of image parts in at least one of the images, each image part including at least one image point, and selecting each measurement zone from contiguous parts determined to have similar characteristics; and for each measurement zone, obtaining a signal representative of at least variations in a time-varying average value of a combination of pixel values at at least a number of the image points for use in determining at least one of a presence and frequency value of at least one peak in a spectrum of a signal corresponding to a frequency of a periodic physiological phenomenon.

The document further discloses several refinements of the method and the system. For instance, the use of photoplethysmographic (PPG) imaging is envisaged.

Photoplethysmographic approaches can be utilized in so-called pulse oximeters which are typically configured for monitoring a subject of interest, for instance for monitoring a patient's blood oxygen saturation. Frequently, mediate detection of (arterial) blood oxygen saturation is referred to as $SpO_2$-measurement.

Recently, remote digital image-based monitoring systems for obtaining patient information or, physiological information of living beings in general, have been described and demonstrated.

As used herein, the term "remotely detected electromagnetic radiation" may refer to radiation components which are sent to a subject of interest from a radiation source and "reflected" by a skin portion of the subject of interest. Since reflection mechanisms in the subject's skin are rather complex and multi-dependent on factors such as wavelength, penetration depth, skin composition, vascular system structure, and further influencing parameters, terms such as "emitted", "transmitted" and "reflected" shall not be understood in a limited way. Typically, a portion of incident radiation may be reflected at the skin's (upper) surface. Furthermore, a portion of incident radiation may penetrate the skin and pass through skin layers. Eventually, at least a portion of the incident penetrating radiation may be absorbed in the skin, while at least another portion of incident penetrating radiation may be scattered in the skin (rather than reflected at the skin's surface). Consequently, radiation components representing the subject of interest which can be captured by a sensor can be referred to as re-emitted radiation.

For remote monitoring and measurement approaches, the use of cameras has been demonstrated. Cameras may particularly involve video cameras capable of capturing sequences of image frames. Preferably, cameras capable of capturing visible light can be used. These cameras may comprise a certain responsivity characteristic which covers at least a considerable portion of a visible light range of the electromagnetic spectrum. As used herein, visible light shall be understood as the part of the electromagnetic spectrum which can be sensed by the human eye without further technical aids.

Remote subject monitoring (e.g., patient monitoring) is considered beneficial since in this way unobtrusive measurements can be conducted. By contrast, non-remote (contact) measurements typically require sensors and even markers to be applied to a skin portion of interest of the subject to be monitored. In many cases, this is considered unpleasant, particularly for long-term monitoring.

It would be therefore beneficial to provide for a system and a method for remote monitoring which further contribute to overcoming the need of obtrusive (contact) measurement.

In this connection, Verkruysse et al., "Remote plethysmographic imaging using ambient light", Optics Express, 16(26), 22 Dec. 2008, pp. 21434-21445 demonstrates that photoplethysmographic signals can be measured remotely with normal ambient light and rather conventional video cameras. However, for remote measurement, huge disturbances have to be expected. Disturbances may involve undesired relative motion between the subject of interest and the monitoring device. Furthermore, varying illumination conditions may adversely influence monitoring reliability and monitoring accuracy. Additionally, since image capturing sensors (e.g., cameras) typically may capture a field of view (e.g., corresponding to a frame size) in which the subject of interest and further surrounding objects are present at the same time, a region of interest has to be selected and should be tracked, if possible. Also for the subject of interest, indicative portions that contain the desired physiological information (e.g., skin portions) and non-indicative portions (e.g., hair and clothes) can be present. Moreover, a plurality of subjects (e.g., patients) can be present in a captured frame. While for obtrusive, tactile measurements these adverse disturbing influences can be minimized, remote, non-obtrusive approaches are facing huge challenges in this regard.

Given that signals of interest may be embedded or, so to say, hidden in slight skin color fluctuations, or even in slightest motion patterns, considerably low signal to noise ratios have to expected, considering the massive adverse impacts of disturbances and distortions which may corrupt the captured data.

In some fields of application, the signal to noise ratio may be even lower. This might be the case when the monitoring or measurement is eventually directed at the determination of derived vital signs information which basically has to be determined in a mediate way on the basis of signals that can be directly obtained from the captured data.

SUMMARY OF THE INVENTION

It is an object of the present disclosure to provide a system and a method for extracting physiological information from remotely detected electromagnetic radiation addressing at least some of the above issues and, moreover, providing further refinements in processing the captured signals such that the desired information can be obtained even under considerably poor monitoring conditions. It would be further advantageous to provide a system and a method which may help facilitating and, more preferably, automatizing the monitoring process. Particularly, the need of human intervention and operation during the monitoring procedure shall be reduced.

In a first aspect of the present disclosure a system for extracting physiological information from remotely detected electromagnetic radiation re-emitted by a subject of interest is presented, the system comprising:

an interface that is configured for receiving a data stream comprising image data representing an observed overall region comprising at least one subject of interest;

a partitioning unit that is configured for defining a plurality of sub regions in the overall region;

a classifier that is configured for classifying the plurality of sub regions into at least one indicative type of region and at least one auxiliary type of region, wherein the at least one indicative type of region comprises at least one indicative region of interest at least partially representing the subject of interest, and wherein the at least one auxiliary type of region comprises at least one reference region; and a data processor configured for processing at least one sub region classified as region of interest, thereby obtaining vital information.

In a second aspect of the present disclosure a system for extracting physiological information from remotely detected electromagnetic radiation is presented, the system comprising:

an interface that receives a data stream comprising image data representing an observed overall region comprising at least one subject of interest;

a partitioning unit that defines a plurality of sub regions in the overall region; and a classifier that classifies the plurality of sub regions into at least one indicative type of region and at least one auxiliary type of region, wherein the at least one indicative type of region comprises at least one indicative region of interest at least partially representing the subject of interest.

The present disclosure is based on the insight that region selection in captured image data is crucial for achieving improved signal derivation results even under considerably poor monitoring conditions. Since typically the subject of interest, but also surrounding objects or even a sensor (or: camera) used during monitoring may move relative to each other typically also the region of interest "moves" or "drifts" over time in the captured image data. So basically, human operation would be required, for instance, an initial selection of the region of interest and consecutive re-selection. Consequently, monitoring accuracy strongly depends on an actual operator's experience.

An automatized classification and selection process may reduce the need of human intervention as to the region of interest (ROI) when monitoring the subject. Selection and classification of sub regions may involve the execution of predefined algorithms and therefore be performed without the necessity of human (or: operator) input. Furthermore, the classifier may be configured not only for detecting "good" sub regions which represent the desired signals and can be utilized during subsequent vital information extraction processes. The classifier can be further utilized for determining rather "non-indicative" sub regions (in terms of the desired signals) which, on the other hand, can serve as reference regions for disturbance and distortion reduction. It is preferred in this connection that the at least one auxiliary type of region comprises at least one reference region.

Consequently, since typically the dominant changes and variations in the reference regions can be attributed to disturbances, such as motion or varying illumination conditions, the reference regions may be utilized and processed in a comparative way so as to further enhance the signal to noise ratio in the region of interest primarily addressed for the extraction of the desired information.

As used herein, image data may involve digital image data, such as at least one sequence of image frames. In some embodiments, the sequence of image frames can also be referred to as a video stream. Preferably, the image data at least partially comprises visible radiation information. Visible radiation may be referred to as visible light. The term visible light can be referred to as the spectral range of radiation which is visible to a human eye. For instance, visible light or visible radiation may involve wavelengths from about 390 to about 750 nanometers (nm). It goes without saying that the term visible light may also refer to sub-ranges of the overall visible light range.

More generally, the image data may comprise optical radiation information. Optical radiation may involve wavelengths from about 100 nanometers (nm) to about 1 millimeter (mm). In some embodiments, the image data may further comprise non-visible radiation information. Non-visible radiation may involve, but is not limited to, infrared (IR) radiation and ultraviolet (UV) radiation. Consequently, the image data may comprise visible and non-visible information (in terms of the human eye's wavelength responsivity).

By way of example, the image data may comprise multiple channel image information. For instance, the image data may be composed of RGB data. RGB may relate to a specific color model or color representation convention. Needless to say, various color model conventions can be utilized for defining the image data. Typically, the image data comprises a wavelength-dependent composition. In this regard, the image data may be composed of several color channels which may involve single (monochrome) color channels and multi-color channels, such as RGB, CMYK and similar color channel or color component conventions. Furthermore, in some embodiments, the image data can be enriched by adding further channels or components, for instance non-visible radiation channels, such as an IR-channel or an UV-channel.

The sub regions to be classified by the classifier can take the same or different size and shape. The sub regions may be arranged adjacent to each other. Alternatively, the sub regions may overlap, at least in part. Alternatively, the sub regions can be spaced apart from each other. Moreover, at least some of the sub regions may be a subset of other sub regions. The size and shape of the sub regions can be flexible and they can be defined differently for each of the image channels described in the paragraph above. In this way the size can be adapted and varied over time so as to further enhance the matching result and therefore the signal quality. Since at least one or some of the sub regions may drift or move in the observed overall region over time, the interrelation between at least some of the sub regions as to size, overlap, position, etc. can vary as well over time.

Consequently, a pattern of classified sub regions can be generated in the observed overall region. Moreover, indicative sub regions can be separated from non-indicative corrupted regions. In this way, a so-to-say heuristic approach can be taken for identifying the indicative regions of interest.

The classifier can be further configured for classifying the plurality of sub regions into an indeterminable type of region. In this way, the classifier may classify the sub regions into the indicative type of region, the auxiliary type of region and the indeterminable type of region. For instance, some sub regions may comprise a representation of an indicative portion of the subject of interest, at least in part, while also comprising non-indicative regions. In this way, the classifier assigns this type of region to the indeterminable type of region so as to avoid cases of doubt.

According to another aspect, the system further comprises a data processor that processes at least one sub region classified as a region of interest, thereby obtaining vital information. Vital information may refer to vital signs information or other physiological parameters. In some embodiments, blood oxygen saturation, pulse rate, respiration rate, and similar vital signals and/or physiological parameters in general, including combinations thereof and derivative parameters, can be detected. The subject of interest to be monitored can be a living being or, at least, a part of a living being like an organ. For instance, humans and animals can be addressed. It goes without saying that the observed overall region does not necessarily have to comprise a full-body representation of the subject of interest. Also a partial representation of the subject of interest can be processed so as to derive vital signs information. In some embodiments, the system can be further configured for processing image data comprising a representation of more than one subject of interest. To this end, known approaches for the detection of individuals can be applied. Consequently, a plurality of subjects of interest can be present in the overall region and processed accordingly for multiple-subject monitoring purposes.

The data processor can further track the at least one indicative region of interest. Particularly, the data processor can be further configured for tracking the at least one region of interest under consideration of at least one sub region classified as reference region. As indicated above, knowledge about the presence and characteristics of at least one reference region can be exploited by the system. Needless to say, also the at least one reference region can be tracked accordingly so as to detect a corresponding shift which may correspond to the shift the at least one region of interest experiences.

According to a further embodiment, the at least one auxiliary type of region comprises at least one reference region, wherein the at least one auxiliary type of region comprises at least one region selected from the group consisting of signal reference region, tracking reference region, relative motion reference region, and combinations thereof.

Each of the reference regions may comprise defined characteristics which may be used when tracking the at least one region of interest. For instance, the tracking reference region may comprise a representation of prominent features of the subject of interest which can be easily tracked. Consequently, for tracking the at least one region of interest, for instance, a relative offset between a tracking reference region and the region of interest can be applied to the tracked tracking reference region over time. By way of example, the tracking reference region may comprise a face representation. Typically, a subject's face can be easily tracked. Furthermore, the region of interest can comprise a forehead portion of the subject to be monitored. In this way, the region of interest can be a subset of the tracking reference region. However, in alternative embodiments, the respective regions can be spaced apart or overlap each other. Motion about respective shift(s) can be exploited for motion compensation measures.

The relative motion reference region may involve a representation of surrounding objects or background objects which typically do not move. In this way, relative motion between the object of interest and stationary objects can be determined. Furthermore, relative motion between the sensor (e.g.: the camera) and the immobile components can be determined.

The signal reference region may involve information which is not of primary interest for subject tracking. The signal reference region may be a region which is close to the at least one region of interest but does not comprise indicative components (in terms of the desired vital signs information). For instance, the signal reference region may comprise a representation of a portion of the subject of interest which is covered by clothes, or even by bedclothes. In this way, the signal reference region is typically exposed to similar or even the same disturbances that affect the at least one region of interest. Consequently, the signal reference region may serve as an indicator or basis measure for the actual noise-dependent corruption of the indicative region of interest. In this way, disturbing influences can be detected and "subtracted" from the at least one indicative region of interest. Consequently, the signal to noise ratio in the at least one region of interest can be enhanced.

It is further preferred if the region of interest comprises a skin portion of the at least one subject of interest. Typically, the desired vital information is embedded in slight fluctuations of skin color, or in minute motion patterns which can be present on the skin. Consequently, at least a considerable portion of the indicative region of interest should comprise a skin representation.

According to another aspect the system further comprises a pattern applicator that applies a pattern of sub regions to the overall region. Particularly, the pattern applicator can be configured for applying an initial pattern of sub regions at the beginning of a monitoring event. The initial pattern may form an initial set of sub regions which can be selected and classified. Alternatively, or in addition, the pattern applicator can be configured for reapplying a pattern of sub regions over the course of a monitoring event. Pattern application can be retriggered in case some quality check values are beyond defined thresholds. The partitioning unit can be configured for defining each sub region of the pattern. Alternatively, the partitioning unit can be configured for defining only some of the sub regions of the pattern. Having classified the defined sub regions, the system can disregard some of the sub regions while data processing can be based on the remaining classified sub regions. According to yet another aspect the classifier further classifies the sub regions according to a classification scheme, wherein the classification scheme comprises at least one classification parameter selected from the group consisting of color model match, feature presence, image contrast, illumination condition, spatial or temporal illumination variation, reflectance, anatomic location, body part presence, vital information accuracy, vital information reliability, and, variations thereof.

By way of example, the color model match classification parameter can be based on skin color models. In this way, skin color presence can be detected. Predefined and/or adaptive skin color models can be utilized. Skin color models can be adjusted in accordance with detected skin portions. Skin color model adaption can be combined with body part detection. The feature presence classification parameter may relate to the presence of blood vessels, fibrous tissue (e.g., scars), prominent skin features, pigmented spots, eye presence, mouth presence, nose presence, face presence, etc.

For instance, the at least one indicative region of interest should be classified on the basis of a classification scheme that strongly relies on skin detection and therefore should match a skin color model. Alternatively, or in addition, the indicative region of interest could be obtained on the basis of body part detection. The body part detection can be as simple as separating between body parts and non-body parts or highly sophisticated as classifying specific anatomic locations (e.g. forehead vs. cheek vs. hand or central vs. peripheral etc.). Furthermore, in some embodiments, the indicative type of region should have low image contrast. Preferably, illumination changes and skin surface reflection (e.g., specular reflection) are not present or only present to a limited extent in the at least one selected indicative region of interest. Furthermore, given that the processing of the indicative region of interest in question leads to reasonable results (for instance, in terms of reliable vital signs information), it becomes more likely that the respective region can be classified as indicative region of interest. In this way, a retrospective classification approach can be applied. For instance, the region in question can be processed so as to derive the heart rate and/or oxygen saturation, and/or derivative signals. Given that these signals are within reasonable ranges, it becomes even more likely that the region in question is an indicative region of interest.

The at least one signal reference region can be used as a reference for ambient noise, such as, for instance, varying ambient illumination conditions. So the respective classification scheme could comprise parameters focusing on considerably high reflectance and considerably low image contrast. Furthermore, the signal reference region may be positioned close to the indicative region of interest.

The at least one tracking reference region mainly serves for tracking purposes. Since motion typically heavily corrupts the signal to noise ratio, motion correction is crucial for sufficiently enhancing the signals of interest. In some embodiments, tracking the indicative region of interest as such is almost impossible since the indicative region of interest merely provides low image contrast. It would be therefore beneficial to select additional regions which may serve as tracking reference region. Typically, regions providing high image contrast can be selected since they can be tracked more easily than low image contrast regions. Consequently, the tracking reference region may involve prominent landmarks and structure. Feature matching approaches for tracking purposes can be applied to these landmarks in the tracking reference regions.

The at least one relative motion reference region may comprise a background representation in the observed overall region. Typically, for some embodiments, the relative motion reference region does not comprise physiological signal components. It is preferred that the relative motion reference region comprises considerably good reflection characteristics. Furthermore, it is preferred that the at least one relative motion reference region provides good image contrast so as to simplify (relative) motion detection.

According to yet another aspect of the present disclosure, the classifier further ranks at least some of the sub regions of the at least one indicative type of region and the at least one auxiliary type of region. In this way, given that more than one sub region can be classified as indicative region of interest or as a respective reference region, among the plurality of classified regions only those of considerably high quality can be selected and regarded during further processing. In this way, processing accuracy and signal to noise ratio can be further enhanced. For instance, only the highest ranked respective region of interest or reference region can be selected for further processing. Alternatively, a relative or absolute share of regions can be selected, such as, for instance, top ten, or top ten percent. Regarding the at least one auxiliary type of region, the ranking can be applied to at least some or each of the at least one signal reference region, the at least one tracking reference region, and the at least one relative motion reference region.

Consequently, given that initially a large number of sub regions can be defined and selected in the overall region, only the most promising regions may be utilized for further processing so as to obtain the desired vital signs information.

Since a plurality of classification parameters can be regarded during classifying and/or ranking the sub regions, a combination of the classification parameters may be selected. Each of the indicative region(s) of interest, the signal reference region(s), the tracking reference region(s), and the relative motion reference region(s) may be linked (or: connected) to a respective distinct combination of classification parameters. Furthermore, weighting factors can be applied to at least some of the classification parameters for forming the combination of classification parameters. In some embodiments, at least some of the classification parameters can be defined as so-called knock-out criteria. In this way, a certain threshold can be defined which may set a minimum requirement for some parameters. For instance, as to the (skin) color model match parameter, knock-out criteria may be defined, since typically it is absolutely necessary to use a skin portion as the at least one indicative region of interest.

According to an even further aspect, the system also comprises at least one sensor capable of sensing electromagnetic radiation in a specific wavelength range, wherein at least one of the at least one sensor is capable of sensing at least one visible light wavelength portion.

As mentioned above, the system of the invention is particularly suited for image-based monitoring making use of optical radiation which can be sensed by standard CCD or CMOS sensors or sensors used for thermal imaging, for instance. The at least one sensor can be capable of capturing a data stream comprising image data. The at least one sensor may have a defined spectral sensitivity or responsivity which is adapted to the optical light wavelength range. The at least one sensor can be embodied as an image sensor, for instance a CCD sensor or a CMOS sensor. Needless to say, also a plurality of sensors can be utilized for sensing electromagnetic radiation so as to capture the image data to be processed.

According to a further development the system comprises a first set of sensors comprising at least one sensor capable of sensing at least one indicative wavelength portion, and a second set of sensors comprising at least one sensor capable of sensing at least one auxiliary wavelength portion.

Further groups of sensors can be envisaged, for instance a third set of sensors which may be capable of sensing at least a further auxiliary wavelength portion. Needless to say, the respective wavelength portions may be arranged adjacent, spaced apart, or at least partially overlapping in the electromagnetic spectrum.

It is further preferred in this connection if the at least one auxiliary wavelength portion is a wavelength portion having a greater penetration depth in skin than the at least one indicative wavelength portion. In this way, the system can make use of the fact that radiation which is capable of deeply penetrating the skin may enhance prominent skin features which can be easily tracked when they are present in the captured image data. The at least one indicative wavelength portion, conversely, can be suitably selected so as to enhance skin color fluctuations which can be highly indicative of the desired vital signs information.

According to yet another embodiment, the second set of sensors comprises at least one relief sensor capable of sensing depth-representative information. In this connection, the system may further comprise a source of electromagnetic radiation, for instance a laser. Such a specific source of electromagnetic radiation can be selectively directed at defined positions in the overall region or the at least one indicative region of interest and eventually captured by the at least one relief sensor. In this way, the overall region, particularly the at least one indicative region of interest, can be scanned so as to obtain relief data. Relief data may be used as a further indicator for tracking the at least one region of interest. Consequently, in addition to wavelength-dependent image data, the system can further capture depth-dependent information based on travel time determination for the defined radiation emitted by the source of electromagnetic radiation combined with the at least one relief sensor. More generally, it may be preferred in this regard if the data stream comprises at least one channel of image data containing depth-representative information.

According to yet another aspect, the data stream comprises at least two channels of image data representing different wavelength ranges. Different wavelength channels can be realized by separate cameras with filters, time-multiplexed illumination, single sensors with tunable filters, etc.

According to still another aspect, the system further comprises a filter arrangement comprising at least one filter for selectively transmitting electromagnetic radiation at defined wavelength portions. The at least one filter can be embodied by means of an optical filter, an electronic filter, a hardware filter and/or a software filter. Also in this way the at least one indicative wavelength portion and the at least one auxiliary wavelength portion can be captured without facing an absolute need of providing more than one set of sensors. By way of example, the filter arrangement can comprise switching filters. In this way, alternatingly, the at least one indicative wavelength portion and the at least one auxiliary wavelength portion can be sensed by the same set of sensors.

In a further aspect of the present disclosure, a method for extracting physiological information from remotely detected electromagnetic radiation is presented, the method comprising steps of:

receiving a data stream comprising image data representing an observed overall region comprising a subject of interest;

defining a plurality of sub regions in the overall region; and classifying the plurality of sub regions into at least one indicative type of region and at least one auxiliary type of region, wherein the at least one indicative type of region comprises at least one indicative region of interest at least partially representing the subject of interest.

Preferably, the method further comprises at least one of the following steps:

applying a pattern of sub regions to the overall region;

classifying the sub regions according to a classification scheme, wherein the classification scheme comprises at least one classification parameter selected from the group consisting of color model match, feature presence, image contrast, illumination condition, spatial or temporal illumination variation, reflectance, body part presence, vital information accuracy, vital information reliability, and combinations thereof;

ranking at least some of the sub regions of the at least one indicative type of region and the at least one auxiliary type of region; and processing at least one sub region classified as region of interest, thereby obtaining vital information.

According to yet another aspect, the method may further comprise the steps of:

processing at least two sub regions classified as indicative region of interest, thereby deriving the same vital parameters from each of those regions; and combining the results from each region so as to obtain a single final vital parameter, wherein the step of combining preferably comprises averaging, weighted averaging, and/or taking the median.

In yet another aspect of the present disclosure, there is provided a computer readable non-transitory medium having instructions stored thereon which, when carried out on a computer, cause the computer to perform the steps of a method in accordance with the present disclosure. The program code (or: logic) can be encoded in one or more non-transitory, tangible media for execution by a computing machine, such as a computer. In some exemplary embodiments, the program code may be downloaded over a network to a persistent storage from another device or data processing system through computer readable signal media for use within the device. For instance, program code stored in a computer readable storage medium in a server data processing system may be downloaded over a network from the server to the device. The data processing device providing program code may be a server computer, a client computer, or some other device capable of storing and transmitting program code.

As used herein, the term "computer" stands for a large plurality of processing devices. In other words, also mobile devices having a considerable computing capacity can be referred to as computing device, even though they provide less processing power resources than standard desktop computers. Furthermore, the term "computer" may also refer to a distributed computing device which may involve or make use of computing capacity provided in a cloud environment. The term "computer" may also relate to medical technology devices, fitness equipment devices, and monitoring devices in general, that are capable of processing data.

Preferred embodiments of the disclosure are defined in the dependent claims. It should be understood that the claimed method and the claimed computer program can have similar preferred embodiments as the claimed device and as defined in the dependent device claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

The following section describes exemplary approaches to remote monitoring of subjects of interest, particularly to remote photoplethysmography (remote PPG), utilizing several aspects of the system and method of the invention. It should be understood that single steps and features of the shown approaches can be extracted from the context of the respective overall approach or embodiment. These steps and features can therefore be part of separate embodiments still covered by the scope of the invention.

Figure 1:
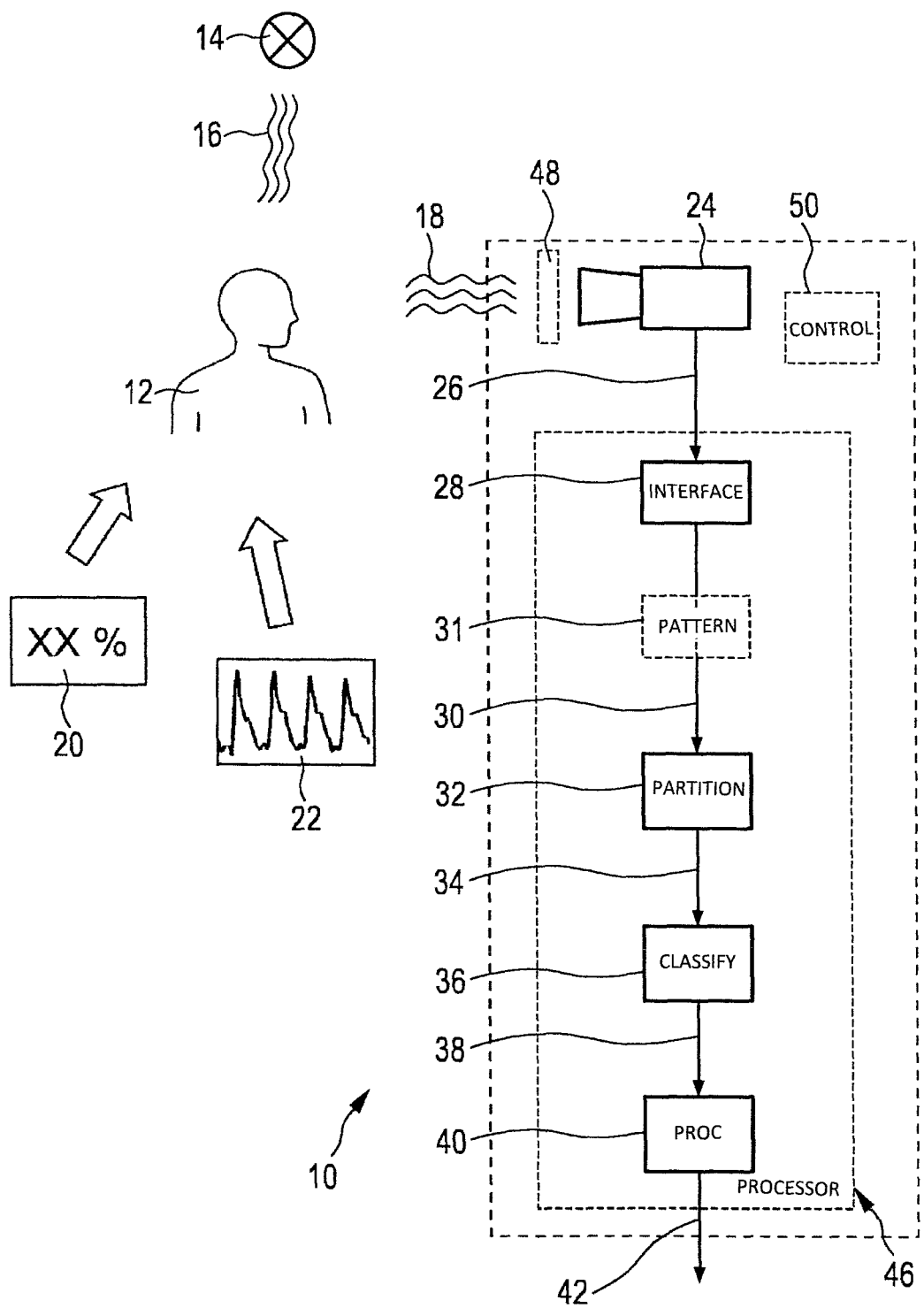
FIG. 1 shows a schematic illustration of a general layout of a system in which the present invention can be used.

FIG. 1 shows a schematic illustration of a system for detecting vital signs information which is denoted by a reference numeral 10. Vital signs information may refer to vital signs as such, but also to further related or derived physiological information which may be obtained through unobtrusive remote monitoring. Particularly, image-based monitoring can be utilized. Image-based monitoring may involve video-based monitoring making use of visible light capturing devices, such as video cameras.

By way of example, the system 10 can be utilized for recording an image sequence comprising image frames representing a remote subject of interest 12 or at least a portion of the subject 12 for remote monitoring, particularly for remote PPG monitoring. In this connection, the subject of interest 12 may be referred to as the whole subject (or: patient) or at least as a portion of the subject, e.g., the face. The recorded image data can be derived from electromagnetic radiation 18 re-emitted by the subject 12. Possibly, under certain conditions, at least a portion of the electromagnetic radiation 18 could be emitted, reflected, or transmitted by the subject 12 itself. Radiation transmission may occur, for instance, when the subject 12 is exposed to strong illumination sources shining through the subject 12. Radiation emission may occur when infrared radiation caused by body heat is addressed and captured. However, for instance for remote PPG applications, a huge portion of electromagnetic radiation 18 to be captured generally can be considered as radiation re-emitted by the subject 12. The subject 12 can be a human being or an animal, or, in general, a living being.

A source of radiation 14, such as sunlight or an artificial radiation source can illuminate the subject 12. The radiation source 14 basically emits incident radiation 16 striking the subject 12. In some embodiments, the source of illumination 14 can be part of the system 10. The system 10 can be configured for eventually deriving vital signs information 20, 22 from the captured image data. Vital signs information 20, 22 may involve, for instance, heart rate, blood oxygen saturation, respiration rate, etc. In some embodiments, derivative vital signs and/or vital parameters can be detected and computed by the system 10. The system 10 can make use of at least one sensor 24, for instance an image sensor. The sensor 24 can be embodied by at least a video camera. The sensor 24 can comprise a CCD camera or a CMOS camera, for instance. Needless to say, a camera utilized by the system 10 can comprise a plurality of (image) sensors 24.

In some embodiments, the system 10 does not necessarily have to comprise a sensor 24. Consequently, the system 10 can also be adapted to process input signals, namely an input data stream 26 comprising image data already recorded in advance and, in the meantime, stored or buffered. The data stream 26 can be delivered to an interface 28. Needless to say, also a buffer means could be interposed between the sensor 24 and the interface 28. Downstream of the interface 28, the input data stream 30 can be delivered to a partitioning unit 32. As indicated above, the input data stream 30 can comprise a sequence of image frames comprising an overall region. The partitioning unit 32 can be configured for defining a plurality of sub regions in the overall region in the input data stream 30.

The system may further comprise a pattern applicator 31 for applying a pattern of sub regions to the overall region in a respective frame. In this way, an initial set of sub regions can be defined. In FIG. 1, the (optional) pattern applicator 31 is represented by a dashed box. In some embodiments, the pattern applicator may comprise a blind operation mode. Given that, only limited information as to respective regions may be available at the beginning of a monitoring event, a possible approach may involve "blindly" applying a pattern having a considerable number of sub regions to the overall region. Probably, a small number of sub regions can be clearly classified and serve as a basis or anchor for further signal processing steps. The pattern applicator 31 can be further configured for varying the number, dimension and position of the to-be-applied sub regions in the overall region. Consequently, a flexible formation and distribution of the sub regions can be achieved.

Selected data 34, for instance, defined sub regions in the overall region, can be delivered to a classifier 36. The classifier 36 can be configured for classifying the plurality of sub regions into at least one indicative type of region and at least one auxiliary type of region. In this way, indicative regions of interest can be identified and selected for further processing. Among the at least one auxiliary type of region, at least some sub regions can be selected which may be used as reference region for the compensation of noise and disturbances in the at least one region of interest.

Classified data 38 (or: classified sub regions) can be delivered to a data processor 40. The data processor 40 can be configured for processing at least one sub region classified as region of interest, particularly under consideration of at least one reference region. For instance, the at least one sub region may comprise a skin representation. Skin color fluctuations can be detected and processed so as to finally obtain the desired vital signs information. Eventually, processed data 42 can be provided to a user or for being further processed. In this connection, an (output) interface can be used. Furthermore, representation devices, such as displays, can be utilized. Some or each of the interface 28, the pattern applicator 31 (if any), the partitioning unit 32, the classifier 36 and the data processor 40 can be combined or implemented in a processing unit 46. The processing unit 46 can be considered as a computing device, or at least, part of a computing device driven by respective logic commands (program code) so as to provide for desired data processing. The processing unit 46 may comprise several components or units which may be implemented virtually or discretely. For instance, the processing unit 46 may comprise a number of processors, such as multi-coprocessors or single core processors. At least one processor can be utilized by the processing unit 46. Each of the processors can be configured as a standard processor (e.g., central processing unit) or as a special purpose processor (e.g., graphics processor). Hence, the processing unit 46 can be suitably operated so as to distribute several tasks of data processing to adequate processors.

The system 10 may further comprise a filter 48 or a respective filter arrangement. The filter 48 can be coupled to the sensor 24. The filter 48 can be utilized for selectively adapting the sensor's 24 responsivity. Furthermore, an imaging control processor 50 can be implemented for suitably operating the sensor 24 and the filter 48. In this way, for instance, image data having a plurality of distinct wavelength compositions can be captured. The imaging control processor 50 may also form a part of the processing unit 46. Alternatively, the imaging control processor 50 may form a part of, or be coupled to, the sensor 24 and/or the source of radiation 14.

Figure 2:
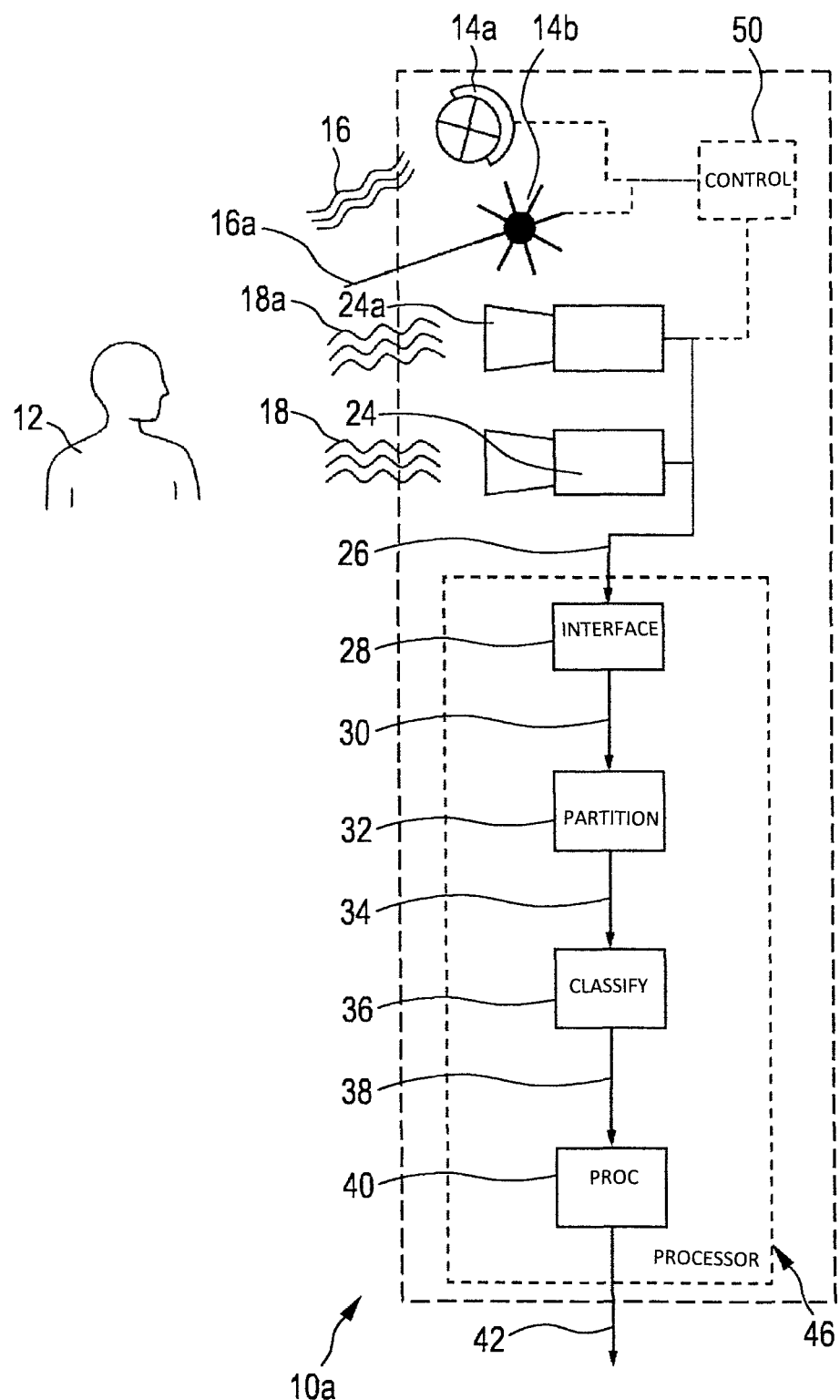
FIG. 2 shows a schematic illustration of an alternative general layout of a system in which the present invention can be used.

FIG. 2 shows a schematic illustration of an alternative system for extracting vital signs information which is denoted by a reference numeral 10a. When compared with FIG. 1, similar or same elements in FIG. 2 are denoted by the same reference numerals. The system 10a shown in FIG. 2 comprises a first sensor 24 capable of sensing electromagnetic radiation 18 having a first wavelength responsivity. Furthermore, a second sensor 24a capable of sensing electromagnetic radiation 18a is provided having a second wavelength responsivity. Needless to say, in some embodiments, more than two sensors 24, 24a can be implemented. For instance, the sensor 24 can be suitably adapted to capture radiation in a wavelength portion in which particularly minute skin color changes due to vascular activities are present. Furthermore, the sensor 24a can be configured for capturing electromagnetic radiation in a wavelength range in which radiation may deeply penetrate skin for enhancing skin features which may be easily tracked. Consequently, using the plurality of sensors 24, 24a, multi-channel input image data can be captured. Furthermore, at least for some of the sensors 24, 24a, multiple channel image input data can be captured by the single sensor as such. For instance, sensing elements can be provided which may address several distinct radiation portions, for instance CCD elements or CMOS elements comprising defined distinct spectral sensitivities.

As indicated by dashed lines, the system 10a may further comprise a radiation or illumination source 14a capable of emitting electromagnetic radiation 16. Furthermore, a distinct source of radiation 14b may be provided, which is also capable of emitting electromagnetic radiation 16a. The source of radiation 14b can be embodied, for instance, by a laser device capable of emitting laser radiation. The image control processor 50 can be configured for controlling the source of radiation 14b so as to selectively control and direct the incident electromagnetic radiation 16a (e.g., a laser beam) to defined points in the overall region, particularly to the subject of interest 12. In this way, a surface (or: relief) can be scanned if at least one of the sensors 24, 24a is capable of sensing reflected (or: re-emitted) portions of the electromagnetic radiation 16a. In this way, the system 10a can be configured for depth-sensing, e.g., via travel time determination. Depth-sensing can be utilized for obtaining relief data. In this way, prominent features of the subject of interest 12 can be detected, for instance a face form or similar prominent features. Consequently, tracking the subject of interest 12 can be further facilitated.

Figure 3:
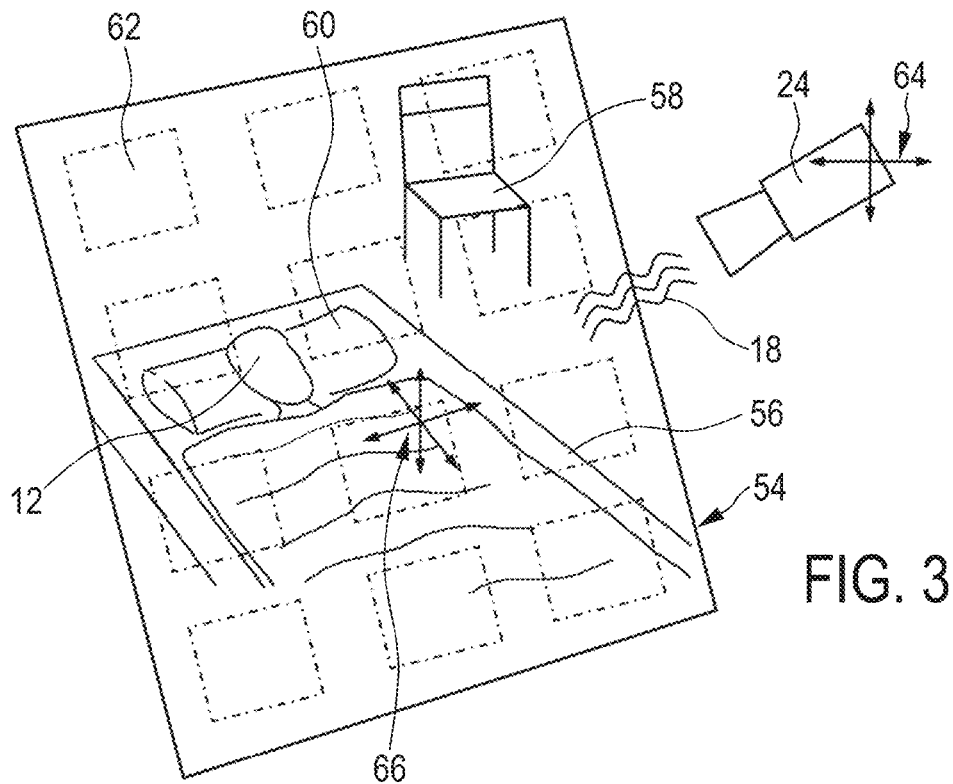
FIG. 3 illustrates an exemplary monitoring arrangement in which a sensor is present which is capable of monitoring an overall region.

FIG. 3 illustrates a monitoring arrangement comprising a to-be-monitored subject 12 which is monitored by a sensor means 24. For instance, the subject 12 can be a patient lying in a bed 56. The sensor 24 can be configured for monitoring or capturing an overall region 54 indicated by a frame in FIG. 3. The overall region may comprise a representation of the subject of interest 12. The overall region 54 can include information acquired by one or more sensors 24 having one or more angles of view. It should be understood that the information from different wavelength ranges can be taken as separate portions of the overall region 54. Furthermore, the overall region may comprise a representation of surrounding objects or background objects, such as the bed 56 and, for instance, a chair 58. The subject 12 can be at least partially hidden or covered, for instance by a blanket or by clothes.

For region classification and data processing, a pattern of sub regions 62 can be applied to the overall region 54. This potentially can result in sub regions having different boundaries for different wavelength ranges. In FIG. 3, a plurality of sub regions 62 is indicated by respective dash-dotted boxes. The plurality of sub regions 62 may serve as a basis for region classifying. In this way, at least some of the sub regions 62 can be assigned to a special type of region so as to be used for a defined distinct purpose when further processing the sub regions 62. For instance, at least some of the to-be-classified sub regions 62 can be used as tracking reference regions. Basically, tracking the subject 12 may contribute to motion compensation and disturbance reduction. Relative motion between the subject 12 and the sensor 24 may heavily corrupt the vital signs information of interest embedded in the captured image data. Furthermore, motion of the subject 12 with respect to surrounding objects 56, 58 may corrupt the detected signals and the make image data processing even more difficult. This applies in particular in remote monitoring environments. In FIG. 3, arrows 64 indicate motion of the sensor 24. Furthermore, arrows 66 indicate motion of the subject 12.

Figure 4:
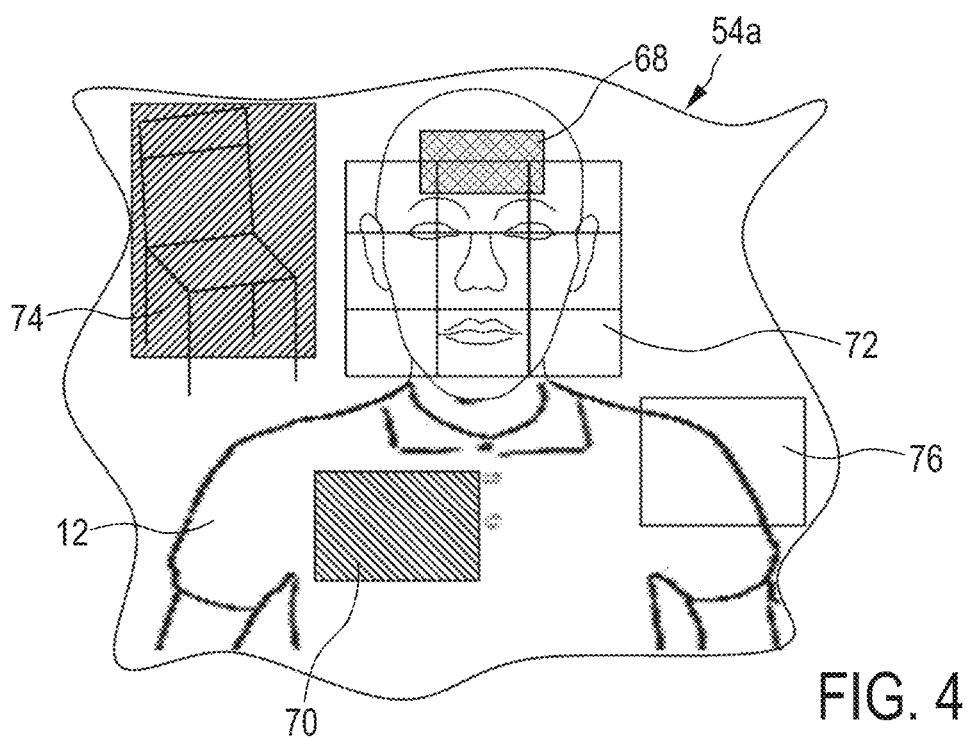
FIG. 4 shows a portion of a monitored overall region in which a subject of interest and surrounding objects are present.

FIG. 4 shows a portion of an overall frame 54a representing a subject 12 to be monitored. In the overall region 54a, at least some of the sub regions 62 (refer to FIG. 3) have been selected and classified for further application during data processing. For instance, an indicative region of interest 68 is present in the overall frame 54a. The indicative region of interest 68 is the region which basically provides the desired signals which are, however, typically superimposed by noise, such as disturbances and distortions due to motion artifacts and varying illumination.

Exemplarily, for some applications, at least some of the following estimations and assumptions can be made so as to define respective classification parameters for the indicative region(s) of interest 68. The region can be skin (tissue), and should provide good signal conditions to derive the desired physiological information. The selection criteria may therefore comprise, for example skin color: the color of region should match the skin-color model, which could be a pre-defined model, or obtained by body part detection (discussed later), image contrast: the region should have low image contrast, illumination (reflection): photometric measurement like blood oxygen saturation basically requires light from the skin area. Any illumination changes could potentially affect the measurement. Reflection on the skin may also influence the photometric measurement. So, preferably, illumination change and reflection should be avoided in that region, and/or physiological parameter (e.g., PPG signal) derived from the region: reasonable parameters may indicate the presence of an indicative region of interest 68. The respective parameters may involve, but are not limited to, pulse rate (e.g. 30-250 bpm, and/or whether it matches with a history of derived pulse-rate-values within physiologically reasonable limits, and/or whether it matches with the pulse-rate of other regions), reasonable oxygen saturation (ratio of ratios corresponds to 50-100% oxygen saturation in all cases, in 99% of the cases to 95-100%, and/or whether it matches with the history of derived oxygen saturation-values within physiological limits), pulsatility amplitude, pulse shape, periodicity, or any other quality metric of the detected signal(s).

Furthermore, a signal reference region 70 is present in the overall region 54a. The signal reference region 70 is considerably close to the indicative region of interest 68. However, preferably the indicative region of interest 68 comprises a skin representation. The signal reference region 70, conversely, preferably comprises a non-skin representation. In this way, it may be assumed that for instance the slight skin color changes of interest are not present in the signal reference region 70. Furthermore, given that still some variations over time are present in the signal reference region 70, it can be assumed that these variations are attributable to varying luminance conditions, etc. In this way, a reference for disturbance compensation is provided.

The above is generally applicable for ambient noises and/or intrinsic system noise, e.g., ambient illumination fluctuations or other noise present in the data stream 26. Alternatively or in addition, the signal reference region(s) 70 can be used as a reference to obtain information about the general illumination condition, e.g. absolute or relative light levels at different wavelengths.

Exemplarily, for some applications, at least some of the following estimations and assumptions can be made so as to define respective classification parameters for the signal reference region 70. Basically, the respective region(s) should be used as a reference for ambient noises, e.g., ambient illumination conditions. So, preferably, only attenuated physiological signal components or even no physiological signal components at all (e.g., no modulation content from blood) are present in the region(s). However, the region(s) should be close to the indicative region(s) of interest 68 for the actual measurement. The selection criteria could involve, for example: good reflection behavior in all relevant wavelengths, and low image contrast in the region(s). In this way, dominant illumination variations are clearly present in the signal reference region(s) 70.

Furthermore, a tracking reference region 72 is present in FIG. 4. The tracking reference region 72 may comprise a representation of prominent features of the subject 12. For instance, face recognition, body part recognition and similar approaches may be taken for identifying and classifying the tracking reference region 72. In some embodiments, the tracking reference region 72 may be reduced in size to the shape of to-be-tracked prominent skin landmarks. Preferably, the tracking reference region 72 can be tracked easily in the overall region 54a over time. Consequently, by maintaining a positional (or: spatial) offset between the indicative region of interest 68 and the tracking reference region 72, the position of the indicative region of interest 68 can be tracked, at least approximately.

Exemplarily, for some applications, at least some of the following estimations and assumptions can be made so as to define respective classification parameters for the tracking reference region 72. Since the relatively weak physiological signals to be detected in the at least one indicative region of interest 68 and to be extracted therefrom can be easily disrupted by motion in that indication region(s), motion correction for that region(s) significantly enhances the signal to noise ratio. However, the at least one indicative region of interest 68 typically comprises poor low image contrast, thus reliably tracking the respective regions is rather difficult. Therefore, additional region(s), the at least one tracking reference region 72, which may contain high image contrast are addressed and used for tracking. It is worth noting that the tracking reference region(s) 72 used for tracking can be generalized as points, e.g., landmark point tracking. Based on tracking the tracking reference region(s) 72, the motion of the at least one indicative region of interest 68 can be corrected. For instance, multiple regions can be initially selected around close to prominent natural landmarks (structure) of the subject 12. These regions then may be continuously tracked in the image sequence. The tracking can involve with several image and video analysis techniques, for example, template matching. Finally, based on the tracking accuracy, optimal one indicative region of interest 68 for vital signs information processing can be selected in/around the best tracked reference region(s) 72.

Alternatively, or in addition, at least one relative motion reference region 74 can be present in the overall region 54a. For instance, the relative motion reference region 74 may comprise a representation of a fixed (immobile) object, for instance, a background object. In this way, a relative motion compensation reference can be obtained. Consequently, if any, sensor motion with respect to the background can be detected and compensated. Furthermore, subject 12 motion with respect to the background can be detected and compensated. In this way, relative motion compensation can be achieved, at least in part. Accordingly, tracking accuracy for the indicative region of interest 68 can be further enhanced.

The relative motion reference region(s) 74 can be utilized in case subject 12 motion occurs. The relative motion reference region(s) 74 can comprise background features which are not connected or coupled to the subject 12. Therefore, there region(s) can be used as a reference for subject motion. Relevant classification parameters may involve strong image contrast, particularly for reliably measuring subject motion.

For illustrative purposes, also an indeterminable region 76 is shown in the overall region 54a in FIG. 4. The indeterminable region 76 may represent a sub region which cannot be classified properly. Preferably, the indeterminable region 76 can be disregarded during further processing. As indicated in FIG. 4, the regions 68, 70, 72, 74, 76 may vary in size. Furthermore, at least some of the regions 68, 70, 72, 74, 76 may overlap each other. In some cases, at least some regions may be formed of subsets of other regions.

It should be further mentioned with particular reference to FIG. 4 that the overall region 54a may also comprise a plurality of at least one of the indicative region of interest 68, the signal reference region 70, the tracking reference region 72, and the relative motion reference region 74.

Figure 5A:
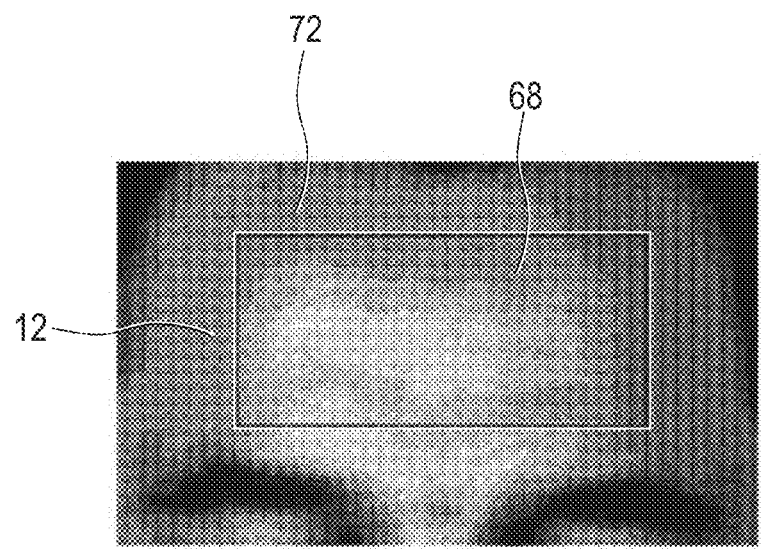
FIGS. 5a, 5b show exemplary image portions which are captured with different wavelength responsivities.
Figure 5B:
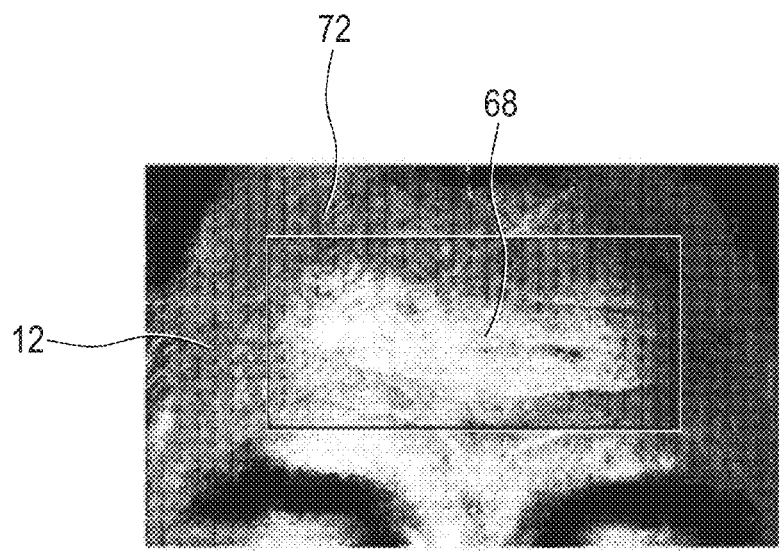

FIGS. 5a and 5b show a captured image, particularly a portion of an overall region. For instance, the respective visible image section may correspond to a tracking reference region 72. Furthermore, as a subset of the tracking reference region 72, an indicative region of interest 68 may be present, which comprises the forehead portion of a subject 12 to be monitored. FIG. 5a may comprise an image which is captured under consideration of a first spectral responsivity for enhancing an indicative wavelength portion. By contrast, FIG. 5b may provide a representation of an image captured under consideration of a second spectral responsivity for enhancing an auxiliary wavelength portion. Typically, the wavelength composition of the image provided in FIG. 5a is suitably adapted for detecting and processing the vital signs information of interest. Alternatively, the wavelength composition of the image provided in FIG. 5b is adapted for enhancing prominent landmarks or features in the tracking reference region 72 for facilitating tracking the subject 12. By way of example, the image shown in FIG. 5b may be based on radiation portions which may deeper penetrate into the subject's 12 skin than the radiation portions used for capturing the image shown in FIG. 5a.

Figure 6A:
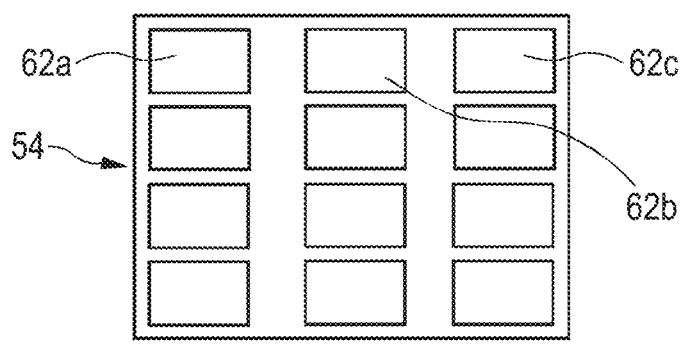
FIGS. 6a-6d show a schematic illustration of an overall region in which a plurality of sub regions is present which may be classified and tracked.

FIGS. 6a, 6b, 6c and 6d show a simplified representation of an overall region 54, 54', 54", 54''' at several stages of an exemplary monitoring and classifying session. As indicated above, at least a subject 12 can be present in the overall region 54. As shown in FIG. 6a, initially, a set of sub regions 62 may be applied to the overall region. In FIG. 6a, exemplarily, some sub regions are indicated by reference numerals 62a, 62b, 62c. Advantageously, a pattern of sub regions 62 can be applied to the overall region 54, for instance by the pattern applicator 31. At least some of the sub regions 62 can be selected and classified.

Figure 6B:
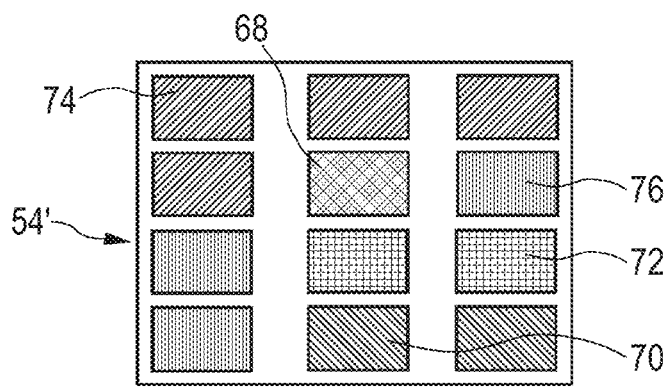

As exemplarily shown in FIG. 6b, the sub regions 62 can be classified into an indicative region of interest 68, a signal reference region 70, a tracking reference region 72, a relative motion reference region 74, and an indeterminable region 76. Having classified some or all of the sub regions 62, classified regions 68, 70, 72, 74 can be adequately used during further processing operations for disturbance compensation and vital signs information detection. Furthermore, at least the indeterminable regions 76 can be disregarded. Further, since not all of the regions 68, 70, 72, 74 have to be considered during further processing operations, also some of these regions can be disregarded. It is preferred in this connection that among each type of region 68, 70, 72, 74 a ranking is established. In this way, particularly best-ranked regions 68, 70, 72, 74 can be selected for further processing.

Figure 6C:
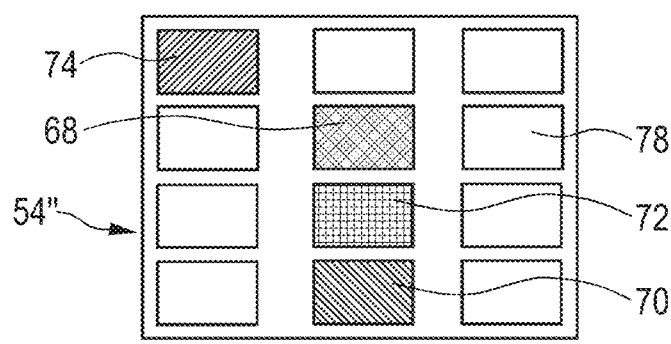

As shown in FIG. 6c, a plurality of regions 78 (blank boxes) is disregarded. The remaining regions (patterned boxes) are selected for tracking and noise compensation purposes and signal derivation measures.

Figure 6D:
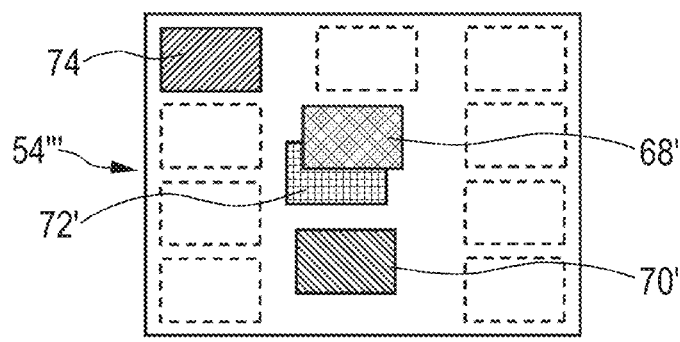

FIG. 6d shows a representation of the overall region 54''', in which at least some of the considered regions 6W, 70', 72' have moved since obviously the subject 12 (not shown) also moved. However, since a high tracking accuracy can be achieved, the indicative region of interest 68' is still identified and can be used for signal processing. In case the system 10 detects that at least one quality and/or accuracy parameter is beyond a reasonable range, pattern application (FIG. 6a), sub region classification (FIG. 6b), and sub region selection (FIG. 6c) can be retriggered in some embodiments.

In some embodiments, the system 10 regularly monitors and controls the quality of the selected regions. To this end, quality scores can be defined on the basis of the classification parameters. A classification scheme may also comprise quality scores. If any or all of the quality scores discussed above is below or beyond a pre-defined threshold, the system may reset the actual measurement and restart the region selection.

Furthermore, classification schemes based on multiple parameters (also: quality metrics) can be defined for each of the regions, e.g., a vector of classification parameters. Some criteria could be defined as "knock-out" criterion. For example, when starting with a set of to-be-classified regions, if there is no region which is likely to be skin, it is not possible to derive vital sign measure at all. On the other hand, it is possible to have an "overall" quality metric which combines the metrics from each indicative region 68 to select a set of indicative region(s) 68 to guarantee the optimal measurement. Furthermore, regarding a combination of different metrics (or: classification parameters), different weights can be given to each metric. For region selection, data history or inputs from other sensors may also be taken into account. For instance, if a vital signal, such as the heart rate, is measured under good conditions for seconds before the system makes a new evaluation of the used ROIs, the system could "stick" more to values of that particular vital signal that were measured earlier and make decisions based on this. Similarly the system could use external (reference) data sources that provide e.g. pulse rate or oxygen saturation from other means (e.g., intermittent measurements from cable less sensors or capacitive ECG). Also in this way accuracy control data can be gathered.

Figure 7:
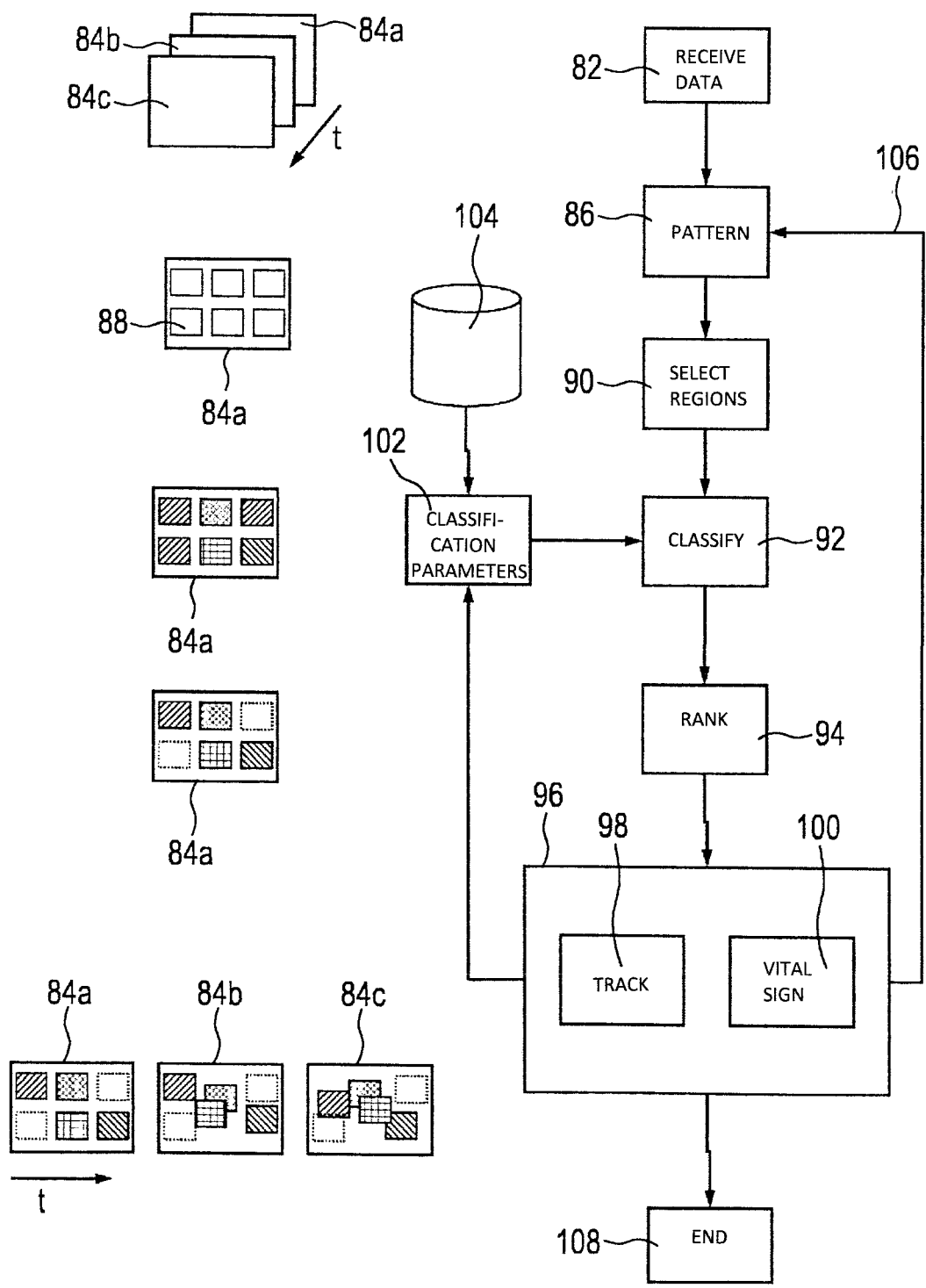
FIG. 7 shows an illustrative block diagram representing several steps of an embodiment of a method in accordance with the present disclosure.

FIG. 7 schematically illustrates a method for extracting physiological information from remotely detected electromagnetic radiation. Initially, in a step 82 imaged data is received, for instance, a sequence of image frames 84a, 84b, 84c. In a subsequent step 86, a region pattern 88 of sub regions is applied to at least a frame 84a. The frame 84a may represent an overall region. In another step 90, at least some sub regions among the pattern 88 are selected for classifying purposes. In some embodiments, both steps 86, 90 can be combined and summarized under the term "defining a plurality of sub regions". A step 92 may stand for a classification process in which at least some of the sub regions are classified into several types of region which may serve for several purposes during data processing.

Another step 94 may follow in which a ranking of classified sub regions (typically belonging to the same type of region) is performed. Preferably, highest ranked regions are used for further processing measures. In this connection, lowest ranked regions can be disregarded during further processing.

Subsequently, a processing step 96 may follow which may comprise a tracking sub step 98 and a vital signs information derivation sub step 100. The sub step 100 may involve signal processing and derivation measures directed at the determination of vital signs information, such as heart rate, heart rate variability, respiration rate, oxygen saturation, etc. The tracking step 98 may also involve tracking at least one or some reference regions. At least some sub regions in the region pattern 88 can be tracked over time, refer to the representation of a frame sequence 84a, 84b, 84c in FIG. 7 including an exemplary pattern representation.

In the step 96, auxiliary information can be obtained which may be helpful in adapting classification parameters and/or a classification scheme. Typically, a set of classification parameters may be provided in a data storage 104. A step 102, which may include classification parameter adaptation may use input from the storage 104. Furthermore, feedback information can be obtained in the processing step 96 so as to adapt the classification parameters and/or the classification scheme accordingly. In this way, the controlling influence over the classifying step 92 can be exerted. Furthermore, the step 96 may provide feedback information 106 which may involve a trigger signal for re-triggering the pattern application step 86. In this way, for instance if massive disturbances and/or faults are detected, the selection and classification of sub regions can be restarted.

Eventually, processed signals, preferably vital signs information-representative signals, can be obtained and provided for representation and/or even further processing measures. At step 108, the process may terminate.

By way of example, the present invention can be applied in the field of healthcare, for instance, unobtrusive remote patient monitoring, in the field of general surveillances, e.g., security monitoring, and in so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. Needless to say, in an embodiment of the method in accordance with the invention, several of the steps described herein can be carried out in changed order, or even concurrently. Further, some of the steps could be skipped as well without departing from the scope of the invention. This applies in particular to several alternative signal processing steps. Several of the disclosed illustrative embodiments can take the form of hardware embodiments, software embodiments, or of embodiments containing both hardware and software elements. Some embodiments are implemented in software which may include firmware and application software.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems. Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution device.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A system for monitoring at least one subject of interest to extract physiological information from remotely detected electromagnetic radiation re-emitted by the at least one subject of interest, comprising:
   an interface configured for receiving a data stream comprising image data representing an observed overall region comprising the at least one subject of interest;
   a display device;
   one or more processors configured to:
      partition the overall region into a first plurality of sub regions of the overall region;
      classify the first plurality of sub regions as (1) a first plurality of sub regions of interest, image data of the data stream corresponding to the first plurality of sub regions of interest including image data to be analyzed to determine a vital sign and being artifacted by noise, motion, and/or illumination variations, and (2) a first plurality of reference sub regions, image data of the data stream corresponding to the first plurality of reference sub regions being indicative of the noise, the motion, and/or the illumination variances and not indicative of the vital sign, wherein classifying the first plurality of sub regions further includes identifying at least one of the first plurality of sub regions as a first tracking sub region, wherein the first tracking sub region is indicative of a first characteristic feature of the subject, rank the first plurality of sub regions of interest;
      select at least one first sub region of interest based on the rank;
      correct the image data of the data stream corresponding to the selected at least one first sub region of interest based on the image data of the data stream corresponding to at least one of the first plurality of reference sub regions;
      determine the vital sign from the corrected image data from the selected at least one first sub region of interest;
      maintain a positional or spatial offset between the selected at least one first sub region of interest and the first tracking sub region;
      over a course of monitoring the subject, in response to quality check values indicative of disturbances or faults exceeding predefined thresholds or a quality and/or accuracy parameter being out of range, partition the overall region into a second plurality of sub regions,
      classify the second plurality of sub regions as (1) a second plurality of sub regions of interest, image data of the data stream corresponding to the second plurality of sub regions of interest including image data to be analyzed to determine the vital sign and being artifacted by the noise, the motion, and/or the illumination variations, and (2) a second plurality of reference sub regions, image data of the data stream corresponding to the second plurality of reference sub regions being indicative of the noise, the motion, and/or the illumination variances and not indicative of the vital sign, wherein classifying the second plurality of sub regions further includes identifying at least one of the second plurality of sub regions as a second tracking sub region, wherein the second tracking sub region is indicative of a second characteristic feature of the subject,
      rank the second plurality of sub regions of interest;
      select at least one second sub region of interest based on the rank;
      correct the image data of the data stream corresponding to the selected at least one second sub region of interest based on the image data of the data stream corresponding to at least one of the second plurality of reference sub regions;
      determine the vital sign from the corrected image data from the at least one selected second sub region of interest;
      maintain a positional or spatial offset between the selected at least one second sub region of interest and the second tracking sub region; and
      control the display device to display the determined vital sign.

2. The system as claimed in claim 1, wherein the one or more processors is further configured to:
   rank the first plurality of reference sub regions, and correct the image data of the data stream corresponding to the selected at least one first sub region of interest based on the image data of the data stream corresponding to a highest ranked first plurality of reference sub regions; or
   rank the second plurality of reference sub regions, and correct the image data of the data stream corresponding to the selected at least one second sub region of interest based on the image data of the data stream corresponding to a highest ranked second plurality of reference sub regions.

3. The system as claimed in claim 1, wherein classifying the first and second pluralities of sub regions includes classifying the first and second pluralities of sub regions according to a classification scheme, wherein the classification scheme comprises at least one classification parameter selected from the group consisting of color model match, feature presence, image contrast, illumination condition, spatial or temporal illumination variation, reflectance, anatomic location, body part presence, vital information accuracy, vital information reliability, and combinations thereof.

4. The system as claimed in claim 1, wherein the data stream comprises at least one channel of image data containing depth-representative information and wherein the one or more processors are further configured to:
   generate a relief image of at least a portion of the overall region,
   identify a prominent feature of the subject from the relief image,
   track motion within the overall region based on motion of the prominent feature.

5. The system as claimed in claim 1, wherein the data stream comprises at least two channels of image data representing different wavelength ranges including a visible wavelength range and a wavelength range that penetrates skin of the at least one subject of interest.

6. A method for extracting physiological information from remotely detected electromagnetic radiation, comprising, with one or more processors:
   receiving a data stream comprising image data representing an observed overall region comprising a subject of interest;
   partitioning the overall region into a plurality of sub regions in a selected pattern; and
   classifying the plurality of sub regions as:

sub regions of interest, wherein image data of the data stream corresponding to the sub regions of interest vary in intensity with a vital sign, reference sub regions, wherein image data of the data stream corresponding to the reference sub regions vary with illumination and do not vary with the vital sign, and a tracking portion of the overall region, wherein image data of the data stream corresponding to the tracking portion vary with movement of the subject;

ranking the sub regions classified as the sub regions of interest;

selecting at least one sub region of interest based on the ranking of the sub regions of interest;

maintaining a positional or spatial offset between the selected at least one region of interest and a characteristic feature of the tracking portion;

correcting image data of the data stream corresponding to the at least one selected sub region of interest based on the image data of the data stream corresponding to at least one of the reference sub regions and the tracking portion;

determining a vital sign from the corrected image data;

controlling a display device to display the determined vital sign;

detecting at least one quality or accuracy parameter and in response to the detected at least one quality or accuracy parameter being beyond a selected range, re-partitioning the overall region into re-partitioned sub regions;

classifying the re-partitioned sub regions;

updating the vital sign based on the re-partitioned sub regions; and controlling the display device to display the updated vital sign.

7. The method as claimed in claim 6, wherein determining the vital sign includes with the one or more processors:

determining a plurality of sub region vital signs based on the corrected image data; and combining the determined sub region vital signs to obtain the vital sign, wherein the combining comprises averaging, weighted averaging, and/or taking a median.

8. A non-transitory computer-readable medium which carries software configured to control a computer to carry out the steps of the method as claimed in claim 6.

9. A photoplethysmographic system comprising:

an interface configured to receive an image data stream from an electromagnetic radiation imaging sensor, the image data stream representing an observed overall region including a subject of interest;

one or more processors configured to:

(a) partition the overall region into sub regions, a component of the image data stream corresponding to each of the sub regions;

(b) classify the sub regions as (1) sub regions of interest and (2) reference sub regions, image data stream components corresponding to the sub regions of interest varying with a vital sign of the subject and noise and changes in lighting, and image data stream components corresponding to the reference sub regions varying with the noise and the lighting;

(c) correct at least one of the sub region of interest components of the image data stream for the noise and the changes in lighting with at least one of the image data stream components corresponding to the reference sub regions;

(d) determine a vital sign from the corrected at least one sub region of interest component of the image data stream;

(e) generate a relief image of a portion of the overall region;

(f) monitor a prominent feature in the relief image for motion;

(g) maintain a spatial offset between the prominent feature and the corrected at least one sub region of interest;

(h) in response to detecting that at least one quality or accuracy parameter is beyond a selected range, return to processor operation (a) and repeat at least operations (a), (b), (c), and (d); and a display controlled by the one or more processors to display the determined vital sign.

10. The system as claimed in claim 9, wherein the corrected at least one of the sub region of interest components of the image data stream comprises a plurality of corrected sub regions of interest components of the image data stream; and wherein the one or more processors is further configured to:

rank the corrected sub region of interest components of the image data stream, and select a highest ranked corrected sub region of interest component of the image data stream;

wherein the vital sign is determined based on the highest ranked corrected sub region of interest data stream component.

* * * * *